United States Patent [19]

Pianetti

[11] Patent Number: 5,147,376
[45] Date of Patent: Sep. 15, 1992

[54] TROCAR NEEDLE LAPAROSCOPY WITH A THREADED TRUNCATED CONE BIT

[76] Inventor: Francesco Pianetti, Via Turati, 22, 20013 Magenta (Prov. of Milan), Italy

[21] Appl. No.: 695,000

[22] Filed: May 2, 1991

[30] Foreign Application Priority Data

May 4, 1990 [IT] Italy ................. 20218 A/90

[51] Int. Cl.⁵ .............................. A61B 17/32
[52] U.S. Cl. .................... 606/170; 606/180; 606/185; 604/264; 604/274; 411/411
[58] Field of Search ............... 128/754; 606/185, 180, 606/167, 170, 73; 604/272, 274, 51, 188, 164, 170, 264, 273, 239; 411/386–387, 394, 411

[56] References Cited

U.S. PATENT DOCUMENTS 4,191,191 3/1980 Auburn .

FOREIGN PATENT DOCUMENTS 0373927 6/1990 European Pat. Off. ............ 606/180

Primary Examiner—C. Fred Rosenbaum
Assistant Examiner—Ronald Stright, Jr.

[57] ABSTRACT

Trocar needle for laparoscopy with a truncated cone bit (1) having at its truncated cone end a cutting blade (2) with a rounded edge arranged obliquely to the axis of the needle and to the plane perpendicular to the axis of the needle which continues with a cutting thread (3) developing in a single turn around the truncated cone tip.

5 Claims, 1 Drawing Sheet

TROCAR NEEDLE LAPAROSCOPY WITH A THREADED TRUNCATED CONE BIT

PRIOR ART

In the laparoscopy art there are normally employed cylindrical needles with a diameter of 9.5 mm having a tapered or pyramidal bit. With the use of these needles it is necessary to take particular precautions to avoid dangerous complications such as lesions to endoabdominal organs and vessels.

For this reason when a laparoscopy is performed a pneumoperitoneum is first performed by introducing into the peritoneal cavity 3-4 liters of $CO_2$.

The pneumoperitoneum causes rising of the front abdominal wall and separation of the internal organs thereof and in particular, if the patient is placed in a slight Trendelemburg's position, the internal organs tend to move to the upper abdominal region.

The trocar needle must be introduced at an angle of 45° in the lower periumbilical seat after sectioning of the skin (in a semicircle around the lower edge of the navel) and the subcutis until reaching the aponeurosis.

In addition the needle must be pushed carefully to avoid sudden deep penetration which could injure the internal organs or large vessels. However, despite all these precautions it is not always possible to avoid traumatic complications of the anatomic structures mentioned above and the complications connected with the pneumoperitoneum. In addition to said normally used needles there has been proposed a trocar needle with tapered end having a bit which continues with a threading around the tapered end thereof (U.S. Pat. No. 4,191,191). The needle is rotated by means of a gear and crank to penetrate.

While having advantages over the above-mentioned widely used needles with a tapered or pyramidal bit, this type of needle has the following drawbacks:
1) because of its complexity it is difficult to use even by an expert laparoscopist because about 10 turns are necessary to introduce it; and
2) pressure of the needle on the abdominal wall although limited is necessary to avoid outward sliding thereof.

Because of these drawbacks this needle has not found any practical application.

SUMMARY OF THE INVENTION

The drawbacks of trocar needles for laparoscopy of the prior art are overcome by the trocar needle with threaded truncated cone bit of the present invention which is characterized in that it has at the truncated cone end a flat cutting blade with rounded edge and arranged obliquely to the axis of the needle and the plane perpendicular to the axis of the needle and which continues with a cutting thread developing in a single turn around the truncated cone bit which allows penetration in the abdominal wall by rotation of a single turn without pressure.

Said trocar needle is very practical and lends itself to wide use, allowing operation with a single turn and no pressure and thus under the safest conditions.

DETAILED DESCRIPTION OF THE INVENTION

The characteristics and advantages of trocar needles with a threaded truncated cone bit for laparoscopy in accordance with the present invention are more fully explained in the following detailed description with reference to the annexed figures of which:

With reference to the reference numbers and letters of the various figures it may be seen that the bit 1 of the trocar needle in accordance with the present invention has at its truncated cone end a blade 2 inclined downward with an inclination of 40°-50° from the axis of the needle (angle $\alpha$) and 40°-50° from the plane perpendicular to the axis (angle $\beta$).

Said blade has a plane surface and rounded cutting edge.

The blade 2 continues from the nearest part with a thread 3 having a cutting edge which develops in a spiral and reaches with a single turn a point opposite the greater base of the truncated cone.

Figure 1:
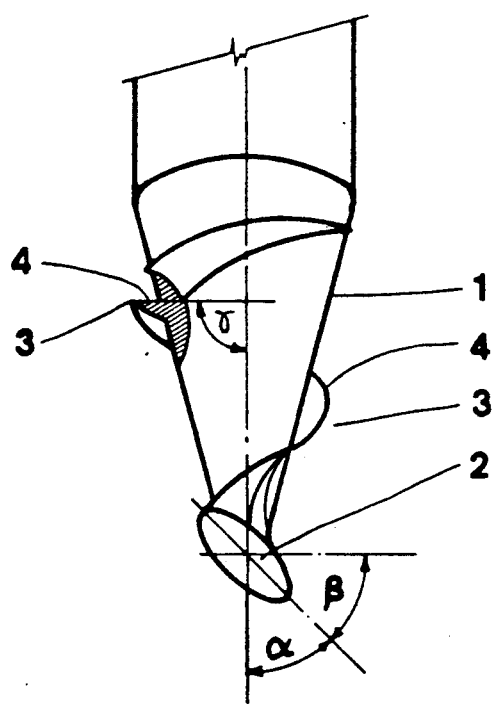
FIG. 1 shows an axonometric representation of the truncated cone bit.
Figure 2:
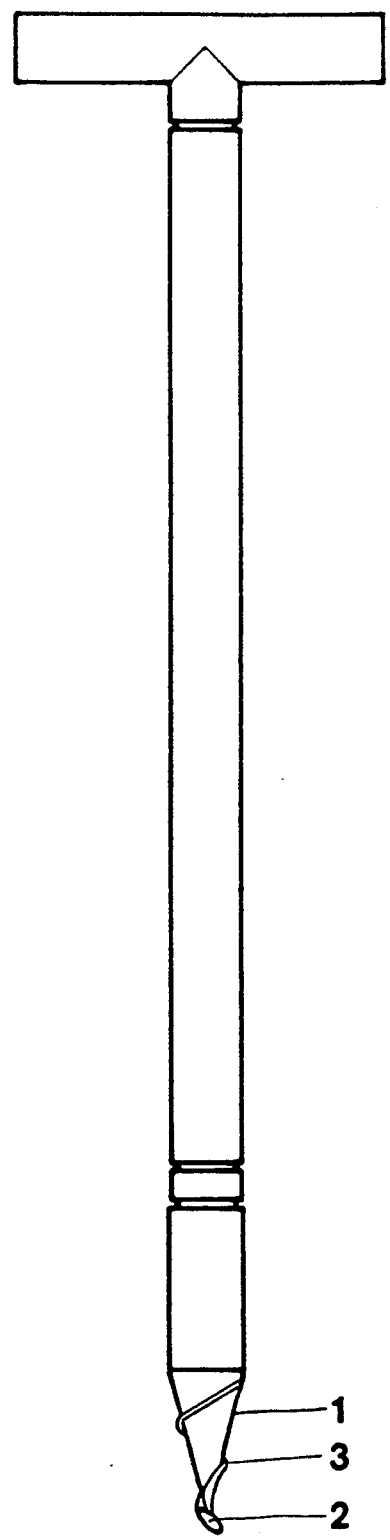
FIG. 2 shows the complete structure of the needle.

The thread 3 has a triangular cross section as may be seen from the sectioned region of FIG. 1 from which it is also seen that the angle formed by the upper face 4 of the thread 3 forms a 90° angle (angle $\gamma$) with the needle axis.

The trocar needle described displays essential advantages for laparoscopy as compared with trocar needles of the known art. When operating with the trocar needle of the invention the operator starts by cutting the abdominal wall with the blade 2 by rotating it a few degrees (about 20°) without applying any pressure and the abdominal wall is then penetrated by rotation of approximately 360° thanks to the development of the thread 3.

The abdominal wall is penetrated without application of pressure during rotation thanks to the profile of the thread 3 which prevents outward slipping of the needle. It may be noted that the profile of the thread 3 allows withdrawal of the partially or totally penetrated needle only by counter-rotation.

When operating with the trocar needle of the present invention the quantity of $CO_2$ necessary for the pneumoperitoneum is halved and the negative effects of endoabdominal pressure on the heart through the diaphragm are cancelled.

In addition lesions to the internal organs of the abdomen and the large vessels are avoided and it is possible to operate with local instead of general anesthesia.

I claim:
1. Trocar needle for laparoscopy with a threaded truncated cone bit (1) characterized in that it has at the truncated cone end a flat cutting blade (2) with rounded edge and arranged obliquely to the needle axis and the plane perpendicular to the needle axis and which continues with a cutting thread (3) developing in a single turn around the truncated cone bit and designed to penetrate the abdominal wall by a single rotation without pressure.

2. Trocar needle in accordance with claim 1 characterized in that the blade (2) forms an angle with the needle axis between 40° and 50°.

3. Trocar needle in accordance with claim 1 characterized in that the blade (2) forms an angle with the plane perpendicular to the needle axis between 40° and 50°.

4. Trocar needle in accordance with claim 1 characterized in that the thread (3) has a triangular cross section.

5. Trocar needle in accordance with claim 1 characterized in that an upper face (4) of the thread (3) forms a 90° angle with the needle axis.

* * * * *